United States Patent [19]

Chang et al.

[11] Patent Number: 4,966,453
[45] Date of Patent: Oct. 30, 1990

[54] FOUR-CHANNEL ANOMALOSCOPE

[75] Inventors: Yin Chang; Yao A. Fu, both of Taipei, Taiwan

[73] Assignee: National Science Council, Taipei, Taiwan

[21] Appl. No.: 390,753

[22] Filed: Aug. 8, 1989

[51] Int. Cl.$^5$ .............................................. A61B 3/06
[52] U.S. Cl. .................................... 351/242; 350/237; 350/174; 362/293
[58] Field of Search ............... 350/237, 220, 221, 242, 350/243, 244, 246, 174; 362/293, 32

[56] References Cited

U.S. PATENT DOCUMENTS

| | | | |
|---|---|---|---|
| 3,801,188 | 4/1974 | Hunt et al. | 351/243 |
| 3,947,099 | 3/1976 | Grolman et al. | 351/242 |
| 4,535,394 | 8/1985 | Dugre | 362/293 |
| 4,765,731 | 8/1988 | Williams | 351/242 |
| 4,798,458 | 1/1989 | Gehrung et al. | 351/242 |

Primary Examiner—Rodney B. Bovernick
Assistant Examiner—J. P. Ryan
Attorney, Agent, or Firm—Cushman, Darby & Cushman

[57] ABSTRACT

A four-channel anomaloscope for detecting the color sense match of the blue cone function and the color weakness or blindness in red and green comprising a housing, optical elements, circuit control means, appropriate computer facilities and software programs wherein the optical elements comprise lighting bulbs, single wavelength interference type filters, 50/50 spectroscopes, a reflective mirror, and photodiodes. The present invention further relates to a method of making the brightnesses of both partitions of the bipartite field produced in the four-channel anomaloscope to coincide with each other.

20 Claims, 5 Drawing Sheets

FOUR-CHANNEL ANOMALOSCOPE

BACKGROUND OF THE INVENTION

Conventional color sense abnormality detectors, also know as anomaloscopes, such as those available from Nagel, Bausch & Lamb, and Double Dichroic Polaroid, comprise only three channels for red, green and yellow light sources in which light rays from the mixed red and green light sources are used to match the yellow light ray, and the red and green light rays are mixed in varied proportions such that ordinary subjects can be divided into two categories, i.e., subjects with normal color sense and those with abnormal color sense. Also, the color sense abnormality detector of the present invention can be used to screen from the subjects having the so-called "normal color sense" those whose red/green color senses are abnormal but who can be classified into groups with color weaknesses in red and green.

According to the principles of conventional color sense abnormality detectors, red and green lights of single wavelength (for different detectors, light sources of different wavelengths may be selected), after being mixed in adjustable proportions, are used to compare with yellow light of fixed wavelength. The brightness of the light from this yellow light source can, of course, be adjusted by the subjects themselves. The comparison is made optically in which the mixed red and green lights are caused to produce a partite and color match (i.e., of uniform color and same brightness) is made with the yellow light of the other partite. The full circle formed of two partitions is referred to as a bipartite field (see FIG. 1). If the colors of both partitions are uniform and the brightnesses the same, the bipartite field becomes a uniform circle showing yellow light. The subjects are allowed free to adjust the proportion of the red and green lights such that when color match is effected different ratios of red to green lights from those for normal persons will be obtained with respect to the subjects possibly due to the fact that they are color weak or blind in red and green.

These conventional detectors, however, can be applied only for detecting cases of color weakness or blindness in that for a subject with glaucoma whose blue cones could be damaged due to the overpressure in his eyes. Then, the subject with weakened function of the blue cones will be unable to perform the color light match which involves such blue cones. This compares to the fact that with a deflated rubber ball, it will not rebound high regardless the physical strength which is used to strike it. In other words, the ball is not sensitive enough to the externally applied force so as to rebound to the corresponding height. Similarly, when the function of the blue cones is weakened, it is impossible to produce a reaction in proportion relative to the stimulation in varied degrees and proportions of the blue light received externally. For such types of subjects, the reaction produced by the stimulation from light with blue component is "inert", then, apparently, it is necessary to carry out a test that is specifically directed to the blue cones.

SUMMARY OF THE INVENTION

The primary object of the present invention is to provide a four-channel anomaloscope which, under normal operating conditions, accurately detects the color sense match involving the blue cone function and which, after being replaced with filters for appropriate wavelengths (between 400–700 nm) and the software programs, can be used for detecting subjects who are color weak or blind in red or green.

Another object of the present invention is to provide a method which is effective for detecting the glaucoma cases, i.e., subjects having damaged blue cones.

To achieve the above objects, an kind of instrument has to be so designed as to find out if a subject is able to sense the slight variation in the blue component of the light. The simplest and the most accurate method is to compare two light rays of the same color and brightness in which one of the light rays is used as the reference light source and the other as the test light source. The two light sources appear to be as one integral light source when they are brought close to each other. The subject, however, will discover the difference therebetween when there are changes in the color components of the test light sources. Thus, the degree of the color component change enabling a subject to notice such a difference represents his sensitivity to a certain light component.

The structure and features of the present invention will become apparent to those skilled in the art from the following description of a preferred embodiments taken in conjunction with reference to the accompanying drawings, in which:

DETAILED DESCRIPTION OF THE INVENTION

Figure 1:
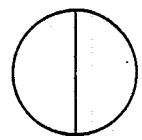
FIG. 1 shows a bipartite field comprising one partite of mixed red and green light rays and another of yellow light ray which is used in a conventional color sense abnormality detector.
Figure 2:
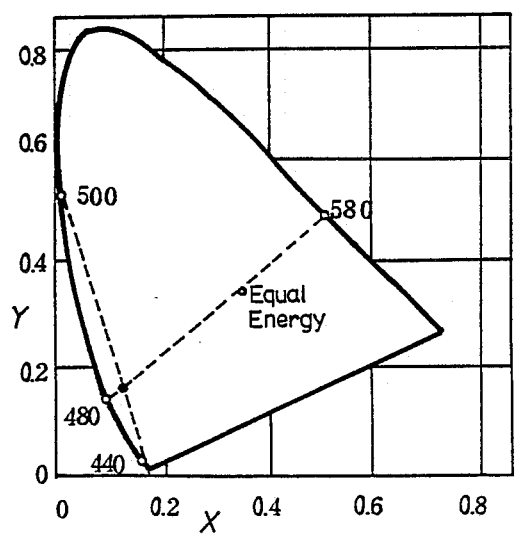
FIG. 2 is a CIE2° chromaticity diagram prepared for the present invention according to the X, Y chromaticity diagram as specified by the Commission International de l'Eclairage in 1931.

According to the CIE2° in chromaticity diagram shown in FIG. 2, light rays having wavelengths of 580 nm, 500 nm, 480 nm and 440 nm are used as the light sources in the four-channel anomaloscope of the present invention while color match is made in accordance with the equation (1):

$$a\ 580\ nm + b\ 480 nm = c\ 440\ nm + d\ 500\ nm \quad (1)$$

Equation (1) is adopted in the present invention primarily for the following reasons:

(a) These two lines intersect in the blue area shown in the CIE chromaticity diagram; and (b) The effect of the macular pigment is reduced (referring to "Optimization of Stimuli for Trit-Anomaloscopy" by J. D. Moreland and J. Kerr; Mod. Probl. Ophthal., Vol 19, pp. 162-166, Karger, Basel, 1978).

The above equation (1) is interpreted as follows: a match is produced between "a" units of 580 nm light rays mixed with "b" units of 480 nm light rays and "c" units of 440 nm light rays mixed with "d" units of 500 nm light rays. That is to say, the "color" and the "brightness" must be identical for the mixed light rays on both sides of the sign of equality in the equation, thus the sign of equality represents the point of intersection of the straight lines a 580 nm+b 480 nm and c 440 nm+d 500 nm, i.e., the matching point. Also, the brightness of the mixed light rays with variable proportions of green (500 nm) and blue (440 nm) components and of the mixed light rays having fixed ratios of yellow (580 nm) and blue (480 nm) components can be maintained at a constant value, i.e., 18 cd/m$^2$ (candlelights/-square meter), by an electronic automatic control system comprising electronic servo circuits.

Figure 3:
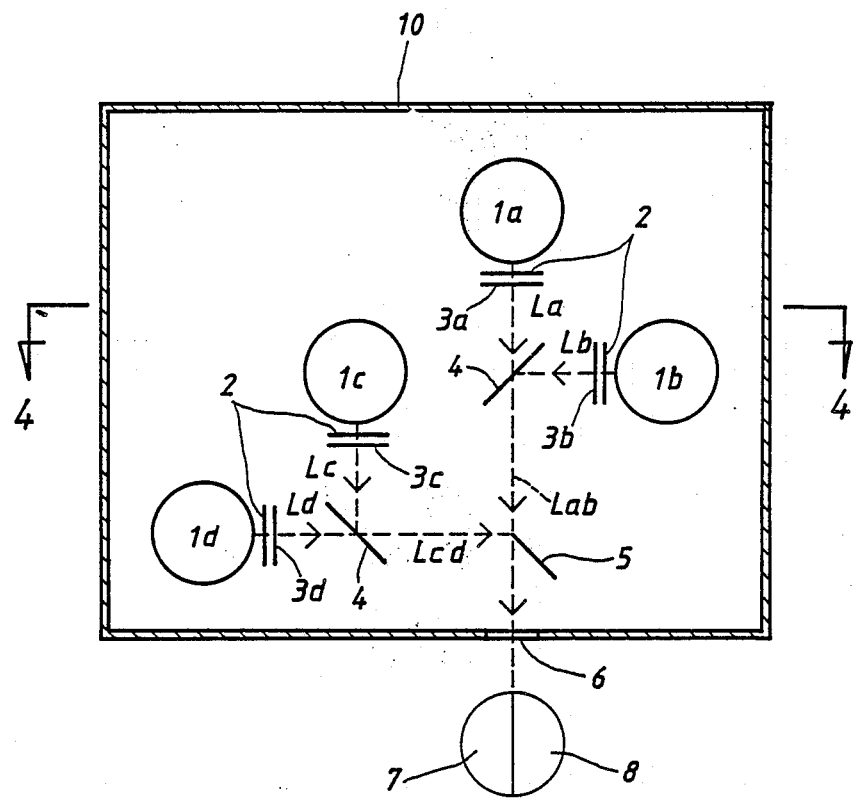
FIG. 3 is a schematic view showing the structure of the optical means of the present invention.

As shown in FIG. 3, the detector of the present invention comprises a housing 10 having four bulbs of PH Series (such as PH-211, PH-212 or PH-213) available from General Electric Company provided therein and designated 1a, 1b, 1c and 1d, respectively, said bulbs being each surrounded by tubular light blocking means (not shown), leaving only an aperture of about 2 cm for the light to pass through, wherein the center distances between individual bulbs 1a-1b, 1a-1c, and 1c-1d are each about 14 cm with the tubular light blocking means having a diameter of about 7 cm and the bulbs 1a, 1b and 1c are so positioned as to form a right angled isosceles triangle with the center of the bulb 1a as the end point at the right angle of the triangle. Four filters of the single wavelength, interference type, designated 3a, 3b, 3c and 3d, are each provided at a position adjacent respective bulbs, the light rays emitted from respective bulbs, after passing through the adjacent filters, becoming the single wavelength light rays having respective wavelengths of 580 nm, 480 nm, 440 nm and 500 nm, the light paths thereof being designated La, Lb, Lc and Ld, respectively. Four hot mirrors 2 are each disposed between individual bulbs and the filters thereof so as to isolate the heat radiation dissipated from the bulbs, thereby to avoid resulting in damage to the filters.

Two 50/50 spectroscopes 4 are each disposed at the intersection of the 500 nm light beam with the 440 nm light beam and at the intersection of the 580 nm light beam with the 480 nm light beam and form an included angle of 45 degrees with respect to the light paths La, Lb and light paths Lc, Ld, respectively, such that the light rays from different light paths are mixed to form into two mixed light paths Lab and Lcd having a mutual angle of 90 degrees. A reflective mirror 5 nearly 100% reflection effective is placed at the intersection of the two mixed light paths and forms an angle of 45 degrees with said two light paths with the reflecting surface oriented toward the direction of the light path Lcd. Therefore, half of the light rays from the mixed light path Lab are blocked by the reflective mirror 5 while the remaining light rays are the other half not blocked by the reflective mirror 5 (i.e., the left half of the mixed light path Lab) which passes through a penetrating hole 6 (about 1 cm in diameter) on the upper portion of the housing 10 to form into the left partite 7 of the bipartite field. In addition, half of the light rays from the mixed light path Lcd are reflected by the reflective mirror 5 to form into another light path which is parallel to but not coincide with the left half side of the mixed light path Lab, and then passes through the penetrating hole 6 to form the right partite 8 of the bipartite field.

Also, the interior of the housing 10 is totally blackened, such that the right half side of the mixed light path Lab blocked by the reflective mirror 5 and the half of the mixed light path Lcd not reflected by the reflective mirror 5 will be absorbed in the blackened interior of the housing 10 without the scattering interference with the light brightness of the bipartite field.

Figure 4:
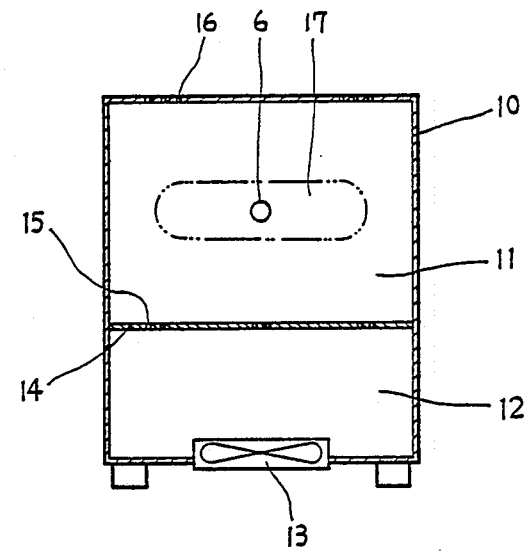
FIG. 4 is a cross section view taken along lines 4—4 of FIG. 3.

Next, as shown in FIG. 4, the housing 10 of the detector is somewhat of a cubic shape having dimensions of approximately 40 cm in length, 36 cm in width and 39 cm in height, the interior thereof being separated into an upper and a lower layers by an intermediate plate 14. The upper layer portion 11 is a light chamber for receiving the optical system of the detector and the lower layer portion 12 has a fan 13 mounted on the bottom for dissipating heat from the instrument. When the fan 13 is running, there is formed in the lower layer portion 12 an air chamber which functions primarily to pump cold air thereinto from the outside and then into the light chamber 11 through a plurality of small holes 15 on the intermediate plate 14. A plurality of vent holes 16 are provided on the top wall of the housing 10 such that the radiation heat produced by the bulbs can be effectively dissipated away from the housing therethrough by the air entering the light chamber 11 so as to achieve excellent heat dissipating results. The area 17 shown in phantom lines in FIG. 4 represents the approximate positions where the bulbs are installed.

Figure 6:
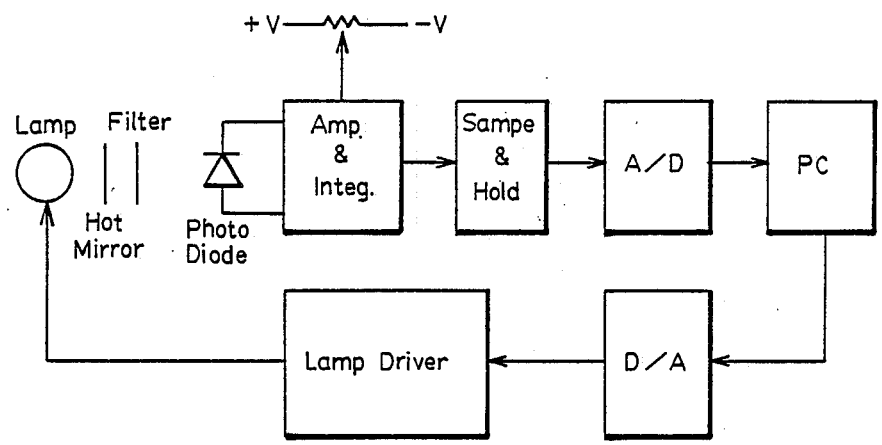
FIG. 6 is a block diagram showing the circuit control system of the present invention.

According to FIG. 6, there is shown the block diagram of the automatic control circuit used in the present invention wherein a photodiode is provided after each of the filters for sensing the intensity of the four light beams of different wavelengths for the purpose of negative feedback automatic control so as to assure that the light rays emerging from each of the channels are absolutely stable.

Given that the intensities of the light rays (brightness) on both side of the sign of equality in the above equation (1) are 2 units (in the present invention the brightness is 18 cd/m$^2$), there must be established the simultaneous equation (2):

$$\left.\begin{array}{l} o \leftarrow a, b, c, d \leftarrow 2 \\ a + b = 2 \\ c + d = 2 \end{array}\right\} \quad (2)$$

Figure 7:
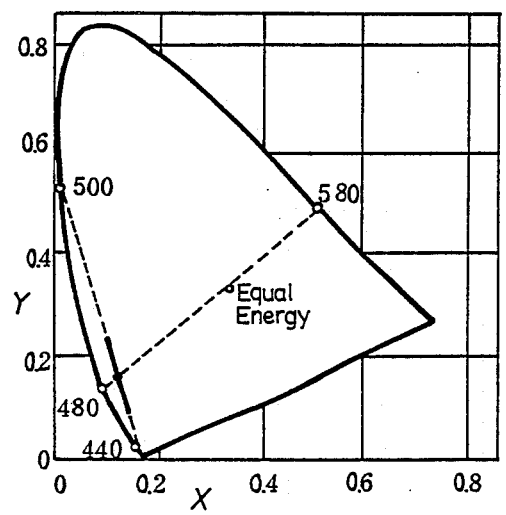
FIG. 7 shows the matching ranges formed, respectively, along the line c of 440 nm and the line d of 500 nm in the CIE2° chromaticity diagram.
Figure 8:
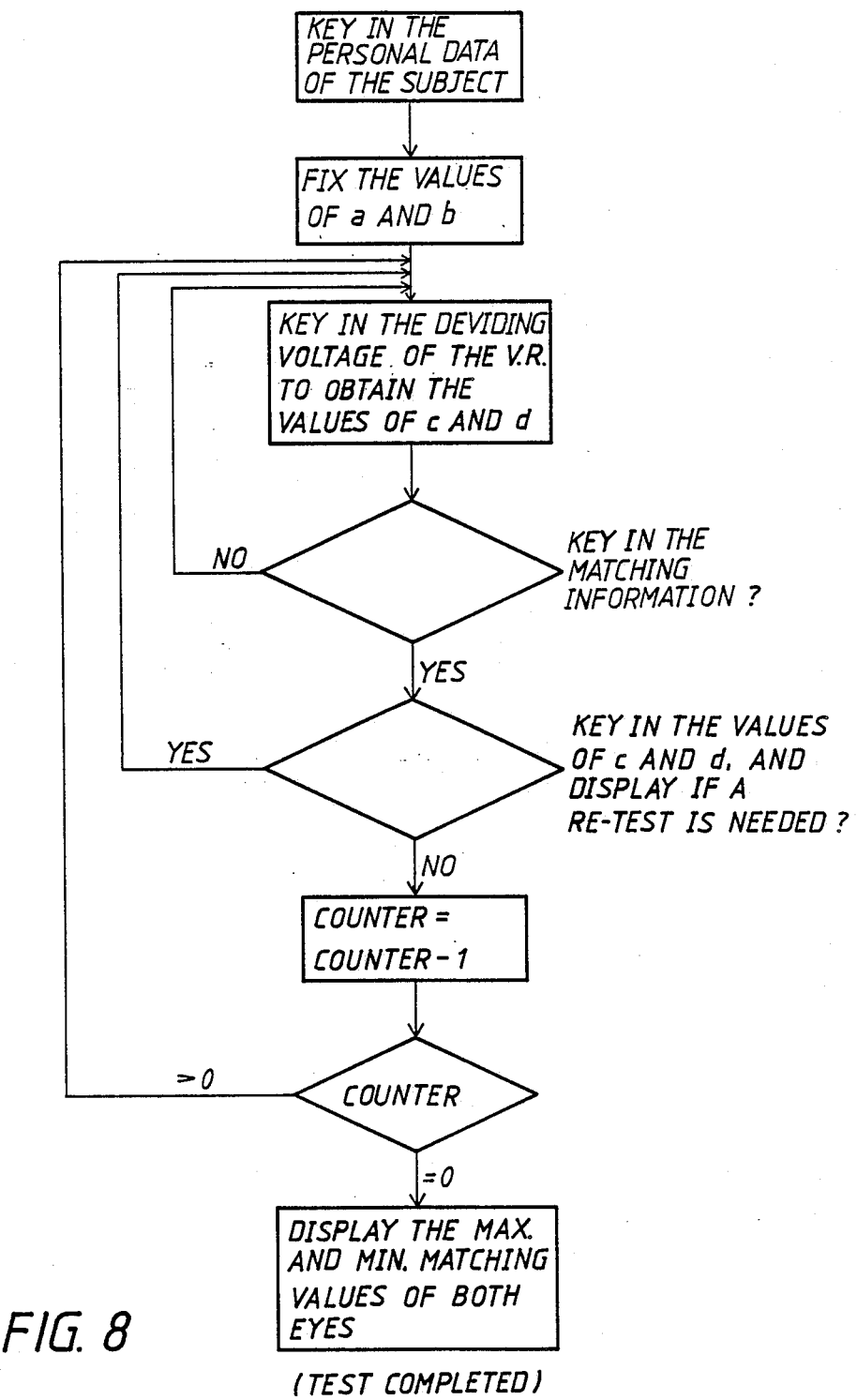
FIG. 8 shows the flow chart of the computer program used in the subject invention.

Assuming the ratio of a to b to be fixed at the matching point such that c and d become adjustable variables, then the above equation (1) can be interpreted as follows: For a subject, any values c and d that have been adjusted may be referred to as a matching value. Moreover, for said subject, according to the equation (2) and through the calculation by the software program, the value d will be automatically adjusted to become 2-c so long as the value c is adjusted. Therefore, a number of values c and d may be obtained for any subject having weakened function of the blue cones. All such values c and d may be referred to as matching values and, then, it is impossible to distinguish any difference between the color variations obtained with light rays of c 440 nm+d 500 nm and that with light rays of a 580 nm+b 480 nm within the range of the values c and d (now the ratio of a to b is fixed at the matching point). Therefore, the sections which connect these matching points on the lines for 440 nm and 500 nm form the matching ranges which are the portions on the line for c 440 nm+d 500 nm shown in solid line in FIG. 7. Furthermore, for subjects with normal functioning blue cones, there are nearly the same values c and d with only slight differences so that only a narrow matching range will be formed on the lines for 440 nm and 500 nm which is the allowance error bound to occur due to the psychophysical tests.

The above data of a, b, c and d are the values obtained by having the light sources amplified through photodiodes and then digitalized by a 12-bit A/D (analog/digital) converter. For example, the full scale of the 12-bit A/D converter is 4096, then the full scale light (18 cd/m$^2$) of each of the channels can be adjusted to 4096 equal parts such that the color is adjusted to be continuous and very precise. Moreover, although the values obtained from the amplifiers are different due to the different sensitivities of the photodiodes to the light rays of various wavelengths, such values, however, can be corrected by means of a chroma meter which has been adjusted according to CIE2° such that the outputs from the amplifiers are of rated values and each of the channels will have a maximal brightness of 18 cd/m$^2$, thus to maintain the brightnesses of both partitions in the bipartite field constant.

According to the detection method of the present invention, a subject is seated at a place about 30 cm from the detector (because of the fovea and the corresponding sight angle of about two degrees, and the bipartite field having a diameter of about 1 cm, the distance of 30 cm can form a sight angle of two degrees), with his chin and forehead placed against a support (compared to the manner in which a subject is seated when being tested with a slit lamp), with one of his eyes covered with an eyepatch while the other looking at the bipartite field. Prior to the test, the adjusting knob will be reset by a tester (personnel conducting the test not the subject) to a standard matching point (of which the numerical value can be read on the monitor of the computer). When starting the test, the subject is asked to look at the bipartite field for about two minutes to adapt his eyes to the brightness thereof and, then, the knob (variable resistor) is rotated slowly clockwise or counterclockwise such that the light rays of the bipartite field in the side of c 440 nm+d 500 nm are shifted toward to the direction of green or blue. When the slight difference between the colors of the two partitions is recognized by the subject, this information will be input into a computer (e.g. IBM PC/AT 16-bit personal computer) by the tester via the keyboard and then the knob will be rotated slowly in the opposite direction such that the colors are shifted toward the other direction passing the standard matching point until again the subject has recognized that the colors are becoming slightly different for the second time and again the information is input into the computer, the values c' and d' being thus recorded by the computer. Said values (c, d) and (c', d') are the values at both end points of a length on the straight lines 440 nm and 500 nm, which length represents the aforementioned matching range. If the above method according to the present invention is retested for a number of times, an accurate and reliable matching range may thus be obtained.

Figure 5:
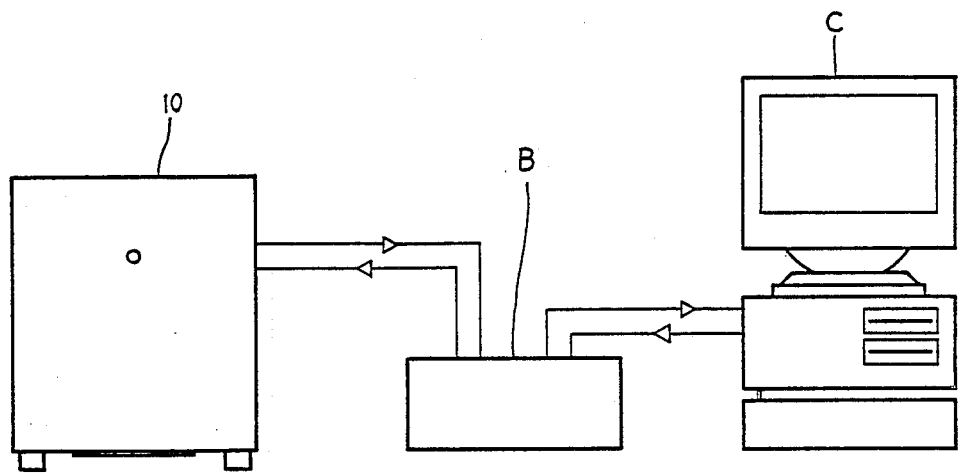
FIG. 5 is a schematic view showing the optical means of the present invention incorporating the circuit control means and a computer equipment.

In the present invention, the brightnesses of the light rays are controlled by means of a controller (B) including electronic servo circuits and the values a and b after being set, are input into the computer (C) in which they are represented in digital form and hence they must be converted to analog signals (i.e., in the form of voltage) by a D/A converter so as to control said electronic servo circuits and to assure that the brightness of the light rays is allowed to be in linear change relation with said analog signals. (see FIGS. 5 and 6).

While a detailed description is made herein with respect to a preferred embodiment of the present invention, various changes and modifications can be made by those skilled in the art without departing from the technical principles of the present invention. It is intended that, however, such changes and modifications are within the scope as defined in the following claims.

We claim:

1. A four-channel anomaloscope comprising:
   a housing;
   an optical means disposed within said housing;
   circuit control means connected to said optical means by connecting wires for controlling the operation of said optical means; and
   a suitable computer and applied software programs which are used in combination with said circuit control means to accurately control the operation of said optical means; wherein
   an intermediate plate is disposed inside said housing which is permeable to air, said intermediate plate separates the interior of the housing into an upper and a lower layers, a side of the housing in the upper layer portion being provided with a penetrating hole, a plurality of small holes being provided on the top wall of the housing for dissipating heat therefrom, the upper layer portion of said housing serving to receive the optical means and forming into a light chamber, and said housing having heat dissipating means mounted on the bottom of the lower layer portion thereof thus forming into an air chamber;
   said optical means comprising:
   a plurality of lighting bulbs;
   a plurality of filters of single wavelength, interference type being each provided at a position adjacent the respective bulbs, the light rays emitted from respective bulbs being adjusted thereby to become light beams of different single wavelengths;
   a plurality of 50/50 spectroscopes being each disposed at the intersection of the two light beams having different wavelengths, and the light beams from the different light paths being mixed thereby;
   a reflective mirror for the light beams which are mixed by said spectroscopes to pass through said penetrating hole on the housing so as to form into a bipartite field; and
   a plurality of photodiodes being provided after said interference type filters for sensing the intensity of the four light beams of different wavelengths for the purpose of negative feedback automatic control.

2. The four-channel anomaloscope as set forth in claim 1 wherein said intermediate plate is provided with a plurality of small air permeable holes.

3. The four-channel anomaloscope as set forth in claim 1 wherein said penetrating hole is provided at the same level as said bulbs.

4. The four-channel anomaloscope as set forth in claim 3 wherein said penetrating hole has a diameter of about 1 cm.

5. The four-channel anomaloscope as set forth in claim 1 wherein said heat dissipating means provided on the bottom of the lower layer portion is a heat dissipating fan.

6. The four-channel anomaloscope as set forth in claim 1 wherein a number of four said lighting bulbs are used.

7. The four-channel anomaloscope as set forth in claim 1 wherein a number of four said single wavelength, interference type filters are used.

8. The four-channel anomaloscope as set forth in claim 7 wherein said filters are used to adjust the light rays emitted from said four bulbs into single wavelength light beams of four different wavelengths.

9. The four-channel anomaloscope as set forth in claim 8 wherein the first one of said filters is used to adjust the wavelength of the light rays emitted from the first bulb adjacent thereto to 580 nm.

10. The four-channel anomaloscope as set forth in claim 8 wherein the second one of said filters is used to adjust the wavelength of the light rays emitted from the second bulb adjacent thereto to 480 nm.

11. The four-channel anomaloscope as set forth in claim 8 wherein the third one of said filters is used to adjust the wavelength of the light rays emitted from the third bulb adjacent thereto to 440 nm.

12. The four-channel anomaloscope as set forth in claim 11 wherein the color and the brightness of the left partite of the bipartite field are maintained constant during the test while the right partite is controlled by means of the circuit control means and the computer equipment so as to have a brightness identical to that of said left partite and a color between pure green (500 nm) and pure blue (440 nm).

13. The four-channel anomaloscope as set forth in claim 8 wherein the fourth one of said filters is used to adjust the wavelength of the light rays emitted from the fourth bulb adjacent thereto to 500 nm.

14. The four-channel anomaloscope as set forth in claim 1 wherein a number of two of said 50/50 spectroscopes are used.

15. The four-channel anomaloscope as set forth in claim 14 wherein the first one of said 50/50 spectroscopes is disposed at the intersection of the light beams of 580 nm and 480 nm wavelengths and the face thereof substantially divides the right angle at which said beams intersect into two equal angles each of 45 degrees so as to form into a first mixed light beam.

16. The four-channel anomaloscope as set forth in claim 14 wherein the second one of said 50/50 spectroscopes is disposed at the intersection of the light beams of 440 nm and 500 nm wavelengths and the face thereof substantially divides the right angle at which said beams intersect into two equal angles each of 45 degrees so as to form into a second mixed light beam.

17. The four-channel anomaloscope as set forth in claim 1 wherein said reflective mirror has one end disposed at the intersection of the light paths of said mixed light beams, the face of said reflective mirror substantially forms an angle of 45 degrees with respect to said mixed light paths with the reflecting surface oriented toward the direction of the second mixed light path such that the right half of the first mixed light beam can be blocked with the left half of said first mixed light beam passing the penetrating hole on said housing to form into the left partite of said bipartite field and that the lower half portion of the second mixed beam is reflected and then passes through said penetrating hole to form into the right partite of said bipartite field.

18. The four-channel anomaloscope as set forth in claim 1 wherein a number of four said photodiodes are used.

19. An Optical means for installing on a four-channel anomaloscope comprising:
a plurality of lighting bulbs;
a plurality of filters of single wavelength, interference type being each provided at a position adjacent the respective bulbs, the light rays emitted from respective bulbs being adjusted thereby to become light beams of different single wavelengths;
a plurality of 50/50 spectroscopes being each disposed at the intersection of the two light beams having different wavelengths, and the light beams from the different light paths being mixed thereby;
a reflective mirror for making the light beams which are mixed by said spectroscopes to form into a bipartite field; and
a plurality of photodiodes being provided after said interference type filters for sensing the intensity of the four light beams of different wavelengths for the purpose of negative feedback automatic control.

20. A method of making the brightnesses of the two partitions of the bipartite field generated in a four-channel anomaloscope to coincide with each other comprising the steps of:
a. first correcting the magnification factor of each of the four channels amplified by the amplifier of a circuit control means to a rated value, by using a chroma meter;
b. converting the analog signals of rated values thus corrected to digital signals by means of a high resolution analog/digital converter;
c. through the operation of the following equations:

$$a\ 580\ nm + b\ 480\ nm = c\ 440\ nm + d\ 500\ nm \qquad (1)$$

$$\left.\begin{array}{l} o \leftarrow a, b, c, d \leftarrow 2 \\ a + b = 2 \\ c + d = 2 \end{array}\right\} \qquad (2)$$

solving to obtain the data a, b, c, and d from the values of said digital signals;
d. said values a and b being maintained constant while said values c and d being changed through the adjustment by rotating a variable resistor; and
e. converting the values a and b, and the values c and d thus corrected to analog signals in voltage form by means of four digital/analog converters to further control the electronic servo circuits of the circuit control means such that the brightnesses of the left and right partitions of said bipartite field are made to coincide with each other.

* * * * *